US009719141B2

(12) United States Patent
Agnello

(10) Patent No.: US 9,719,141 B2
(45) Date of Patent: Aug. 1, 2017

(54) PROGNOSTIC MARKER FOR CRYOGLOBULINEMIC VASCULITIS AND B CELL MALIGNANCIES IN HCV INFECTED PATIENTS

(75) Inventor: Vincent Agnello, Weston, MA (US)

(73) Assignee: Vincent Agnello, Weston, MA (US)

( * ) Notice: Subject to any disclaimer, the term of this patent is extended or adjusted under 35 U.S.C. 154(b) by 0 days.

(21) Appl. No.: 13/581,759

(22) PCT Filed: Feb. 28, 2011

(86) PCT No.: PCT/US2011/026455

§ 371 (c)(1),
(2), (4) Date: Nov. 6, 2012

(87) PCT Pub. No.: WO2011/109285

PCT Pub. Date: Sep. 9, 2011

(65) Prior Publication Data

US 2013/0052206 A1 Feb. 28, 2013

Related U.S. Application Data

(60) Provisional application No. 61/309,161, filed on Mar. 1, 2010.

(51) Int. Cl.

| | |
|---|---|
| ***C12Q 1/68*** | (2006.01) |
| ***C07H 21/02*** | (2006.01) |
| ***C07H 21/04*** | (2006.01) |
| ***G01N 33/576*** | (2006.01) |
| ***G01N 33/574*** | (2006.01) |
| ***G01N 33/68*** | (2006.01) |
| ***C07K 16/28*** | (2006.01) |

(52) U.S. Cl.

CPC ............ *C12Q 1/6886* (2013.01); *C07K 16/28* (2013.01); *G01N 33/5767* (2013.01); *G01N 33/57426* (2013.01); *G01N 33/686* (2013.01); *G01N 2800/328* (2013.01); *G01N 2800/52* (2013.01)

(58) Field of Classification Search

None

See application file for complete search history.

(56) References Cited

U.S. PATENT DOCUMENTS

| | | | |
|---|---|---|---|
| 2005/0234224 | A1 | 10/2005 | Shihabi |
| 2008/0026952 | A1 | 1/2008 | Dietrich et al. |

FOREIGN PATENT DOCUMENTS

| | | |
|---|---|---|
| CN | 1856508 A | 11/2006 |

OTHER PUBLICATIONS

Abel et al, Hepatitis C Virus Infection in Type II Mixed Cryoglobulinemia, Arthritis & Rheumatism, 36(10): 1341-9, 1993.*

De Re et al. International Journal Cancer. 2000. 87: 211-216.*
Knight et al. Blood. May 2001. 97: 3319-3321.*
Franzen et al (British J Haematology. 1995. 90: 548-552.*
Borretzen et al. J. Immunology. 1995. 155: 3630-3637.*
GenBank Accession No. AY0559634, Mar. 14, 2002, National Center for Biotechnology Information, National Library of Medicine (Bethesda, MD, USA).*
GenBank Accession No. AY0059635, Mar. 14, 2002, National Center for Biotechnology Information, National Library of Medicine (Bethesda, MD, USA).*
G.B. Knight, et al. "Detection of WA B cells in Hepatitus C virus infection." In Arthritis & Rheumatism vol. 62(7):2152-2159 (Jul. 2010.).
De Re V, et al. "Characterization of antibodies directed against the immunoglobulin light kappa chain variable chain region(VK) of hepatitis C virus-related type-II mixed cryoglobulinemia and B-cell proliferations." In Ann. N. Y. Acad. Sci. vol. 1173:152-160 (Sep. 2009.).
L. Buonaguro, et al. "Immune signatures in human PBMCs of idiotypic vaccine for HCV-related lymphoproliferative disorders." In Journal of Translational Medicine vol. 8:18 (Feb. 19, 2010.).
Knight et al. "Human Rheumatoid Factor Cross-Idiotypes." *J. Exp. Med.* 178(1993):1903-1911.
Agnello et al. "A Role for Hepatitis C Virus Infection in Type II Cryoglobulinemia." *New. Eng. J. Med.* 327.21(1992):1490-1495.
Agnello et al. "Human Rheumatoid Factor Crossidiotypes. I. WA and BLA are Heat-Labile Conformational Antigens Requiring Both Heavy and Light Chains." *J. Exp. Med.* 164.5(1986):1809-1814.
Agnello. "Therapy for Cryoglobulinemia Secondary to Hepatitis C Virus: The Need for Tailored Protocols and Multiclinic Studies." *J. Rheumatol.* 27.9(2000)2065-2067.
Carbonari et al. "Hepatitis C Virus Drives the Unconstrained Monoclonal Expansion of VH1-69-Expressing Memory B Cells in Type II Cryoglobulinemia: A Model of Infection-Driven Lymphomagenesis." *J. Immunol.* 174.10(2005):6532-6539.
Casato et al. "Predictors of Long-Term Response to High-Dose Therapy in Type II Cryoglobulinemia Associated With Hepatitis C Virus Infection." *Blood.* 90.10(1997):3865-3873.
Casato et al. "Regression of Lymphoproliferative Disorder After Treatment for Hepatitis C Virus Infection in a Patient With Partial Trisomy 3, Bcl-2 Overexpression, and Type II Cryoglobulinemia." *Blood.* 99.6(2002):2259-2261.
Charles et al. "Clonal Expansion of Immunoglobulin M+CD27+ B Cells in HCV-Associated Mixed Cryoglobulinemia." *Blood.* 111. 3(2007):1344-1356.
De Rosa et al. "Observations on Cryoglobulin Testing: I. The Association of Cryoglobulins Containing Rheumatoid Factors with Manifestation of Cryoglobulemic Vasculitis." *J. Rheumatol.* 36.9(2009):1953-1955.
Franzin et al. "Clonal B-Cell Expansions in Peripheral Blood of HCV-Infected Patients." *Br. J. Haematol.* 90.3(1995):548-552.
GenBank Accession No. U03400, Aug. 11, 2010.
GenBank Accession No. U03401, Aug. 11, 2010.
Giordano et al. "Risk of Non-Hodgkin Lymphoma and Lymphoproliferative Precursor Diseases in US Veterans With Hepatitis C Virus." *JAMA.* 297.18(2007):2010-2017.
Hermine et al. "Regression of Splenic Lymphoma With Villous Lymphocytes After Treatment of Hepatitis C Virus Infection." *N. Engl. J. Med.* 347.2(2002):89-94.

(Continued)

*Primary Examiner* — Carla Myers

(74) *Attorney, Agent, or Firm* — Mintz Levin Cohn Ferris Glovsky and Popeo, P.C.; Ingrid A. Beattie

(57) ABSTRACT

The invention provides methods and compositions for early diagnosis and treatment of a disease associated with a specific antibody by employing the detection of a cross-idiotypic epitope on the specific antibody to detect the cells that produce the antibody before the development of clinical symptoms of the disease.

5 Claims, 2 Drawing Sheets

(56) References Cited

OTHER PUBLICATIONS

Invernizzi et al. "Secondary and Essential Cryoglobulinemias. Frequency, Nosological Classification, and Long-Term Follow-Up." *Acta Haematol.* 70.2(1983):73-82.
Klein et al. "Evidence for a Large Compartment of IgM-Expressing Memory B Cells in Humans." *Blood.* 89.4(1997):1288-1298.
Kunkel et al. "Cross-Idiotypic Specificity Among Monoclonal IgM Proteins With Anti-γ-Globulin Activity." *J. Exp. Med.* 137.2(1973):331-342.
Liu et al. "Innnnunophenotype and Ultrastructure of B-Cell Lymphoproliferative Disorder With Cytoplasmic Projection." *J. Huazhong Univ. Sci. Technolog. Med. Sci.* 23.3(2003):236-238.
Lunel et al. "Cryoglobulinemia in Chronic Liver Disease: Role of Hepatitis C Virus and Liver Damage." *Gastroenterology.* 106.5(1994):1291-1300.
Mackworth-Young et al. "Idiotypic Markers of Polyclonal B Cell Activation. Public Idiotypes Shared by Monoclonal Antibodies Derived from Patients with Systemic Lupus Erythematosus or Leprosy." *J. Clin. Invest.* 79.2(1987):572-581.
Marasca et al. "Immunoglobulin Gene Mutations and Frequent Use of VH1-69 and VH4-34 Segments in Hepatitis C Virus-Positive and Hepatitis C Virus-Negative Nodal Marginal Zone B-Cell Lymphoma." *Am. J. Pathol.* 159.1(2001):253-261.
Mazzaro et al. "Regression of Monoclonal B-Cell Expansion in Patients Affected by Mixed Cryoglobulinemia Responsive to α-Interferon Therapy." *Cancer.* 77.12(1996):2604-2613.
Monti et al. "Cryoglobulinaemias: A Multi-Centre Study of the Early Clinical and Laboratory Manifestations of Primary and Secondary Disease." *Q. J. Med.* 88.2(1995):115-126.
Ohsawa et al. "Risk of Non-Hodgkin's Lymphoma in Patients With Hepatitis C Virus Infection." *Int. J. Cancer.* 80.2(1999):237-239.
Quinn et al. "The B-Cell Receptor of a Hepatitis C Virus (HCV)-Associated Non-Hodgkin Lymphoma Binds the Viral E2 Envelope Protein, Implicating HCV in Lymphomagenesis." *Blood.* 98.13(2001):3745-3749.
Saadoun et al. "Splenic Lymphoma With Villous Lymphocytes, Associated With Type II Cryoglobulinemia and HCV Infection: A New Entity?" *Blood.* 105.1(2005):74-76.
Schifferli et al. "Hepatitis C Virus Infection, Cryoglobulinemia, and Glomerulonephritis." *Adv. Nephrol. Necker Hosp.* 24(1995):107-129.
Stein et al. "Monocytoid B Cells are Distinct From Splenic Marginal Zone Cells and Commonly Derive from Unmutated Naïve B Cells and Less Frequently From Postgerminal Center B Cells by Polyclonal Transformation." *Blood.* 94.8(1999):2800-2808.
Suarez et al. "Splenic Lymphona With Villous Lymphocytes, Mixed Cryoglobulinemia and HCV Infection: Deciphering the Role of HCV in B-Cell Lymphomagenesis." *Digest. Liver Dis.* 39.S1(2007):S32-S37.
Volk et al. "Public Health Impact of Antiviral Therapy for Hepatitis C in the United States." *Hepatol.* 50.6(2009):1750-1755.
Zemlin et al. "The Diversity of Rearranged Immunoglobulin Heavy Chain Variable Region Genes in Peripheral Blood B Cells of Preterm Infants is Restricted by Short Third Complementarity-Determining Regions but not by Limited Gene Segment Usage." *Blood.* 97.5(2001)1511-1513.
Imura et al., NEFA/nucleobindin-2 is a target autoantigen of the anti-WA antibody and is associated with transfer RNA. Mod Rheumatol. Sep. 2012;22(5):685-94.
Spertini et al., Prevention of murine cryoglobulinemia and associated pathology by monoclonal anti-idiotypic antibody. J Immunol. Oct. 15, 1989;143(8):2508-13.
Villano et al., Persistence of viremia and the importance of long-term follow-up after acute hepatitis C infection. Hepatology. Mar. 1999;29(3):908-14.

* cited by examiner

PROGNOSTIC MARKER FOR CRYOGLOBULINEMIC VASCULITIS AND B CELL MALIGNANCIES IN HCV INFECTED PATIENTS

RELATED APPLICATIONS

This application is a national stage application, filed under 35 U.S.C. §371, of International Application No. PCT/US2011/026455, filed Feb. 28, 2011, which claims the benefit of provisional application U.S. Ser. No. 61/309,161, filed Mar. 1, 2010, the contents of which are incorporated by reference in its entirety.

FIELD OF THE INVENTION

This invention relates generally to methods for early diagnosis and treatment of disease associated with hepatitis C virus infection.

BACKGROUND OF THE INVENTION

An uncommon manifestation of hepatitis C virus (HCV) infection is systemic vasculitis associated with Type II cryoglobulinemia (cryoglobulinemic vasculitis), a proliferative B cell disorder that transforms to B cell malignancy in 5-10% of patients. The duration of HCV infection required for development of cryoglobulinemic vasculitis is not well delineated, but appears to be a decade or more. As the majority of people infected do not experience any symptoms during this prolonged period prior to onset of symptoms of cryoblobulinemic vasculits, early diagnosis of cryoglobulinemic vasculitis or the associated B cell malignancies is rarely made. Since hepatitis C patients are not likely to be treated before they become symptomatic, there is a need in the art for the discovery of prognostic markers that aid in the early diagnosis of cryoglobulinemic vasculitis and the associated B cell malignancies in HCV-infected patients.

SUMMARY OF THE INVENTION

The invention includes methods for early diagnosis and treatment of a disease associated with a specific antibody by employing the detection of a cross-idiotypic epitope on the specific antibody to detect the cells that produce the antibody before the development of clinical symptoms of the disease. Specifically, the invention provides a method for early diagnosis of cryoglobulinemic vasculitic or B cell malignancies associated with Type II cryoglobulinemia using B cell clonal expansion (BCE) analyses of patients with hepatitis C virus (HCV) infection before such patients develop these complications of the infection. Also described herein are methods of treatment employing antibodies to the detected cross-idiotype antigen. The invention is based on the surprising discovery that detection of WA B cells in asymptomatic HCV-infected patients is a marker for the development of cryoglobulinemic vasculitis and the associated B cell malignancies.

Described herein are methods for identifying a subject who is at risk of developing cryoglobulinemic vasculitis and B cell malignancy associated with HCV. First, a sample is provided from a subject infected with HCV. A suitable sample is a biological fluid comprising whole blood. If WA cross-idiotype positive (Xid+) B cells are detected in the sample, the subject is identified as one who is at risk of developing cryoglobulinemic vasculitis and B cell malignancy associated with HCV. In one aspect, the subject is identified early. Preferably, the early-identified subject is identified after initial HCV infection, but prior to the manifestation of symptoms associated with cryoglobulinemic vasculitis or B cell malignancies.

In one aspect, the WA Xid+ B cells are detected by identifying an immunoglobulin nucleic acid sequence from a clonally expanded B cell population, wherein the immunoglobulin nucleic acid sequence is associated with WA Xid. The immunoglobulin nucleic acid sequence associated with WA Xid comprises IgH V1-69, or IgHV V 3-7 or related germ line genes, VK325 or VK 328, JH4 or JH3, Jk1, and a D region consensus sequences comprising SEQ ID NO: 1 (consensus 1) or SEQ ID NO: 2 (consensus 2).

Alternatively, the WA Xid+ B cells are detected with an isolated anti-WA Xid antibody. Optionally, the isolated anti-WA Xid antibody is attached to a label. In one aspect, the label is a fluorescein isothiocyanate (FITC) label or a phycoerythrin (PE) label. The WA Xid+ B cells are detected via immunostaining or flow cytometric analysis. In one aspect, the method further comprises detecting in the sample a CD $11C^+$ cell with an anti-CD 11c antibody.

Also provided are methods for identifying a subject who is at risk of developing cryoglobulinemic vasculitis or B cell malignancy associated with HCV infection. First, a nucleic acid sample is provided from clonally expanded B cells of an HCV-infected patient to detect immunoglobulin nucleic acid sequences associated with WA Xid, wherein said sequences comprise IgH V1-69 or IgHV3-7 or related germ line genes, VK325 or VK328, JH4 or JH3, and Jk1. Subsequently, a sequence comprising SEQ ID NO: 1 or SEQ ID NO: 2 is detected in the sample. The development of an HCV-infection associated cryoglobulinemic vasculitis or associated B cell malignancy is prognosed if SEQ ID NO: 1 or SEQ ID NO: 2 is present in the HCV-infected patient-derived nucleic acid that contains the IgH and VK sequences associated with WA Xid. In one aspect, the patient lacks a clinical symptom of cryoglobulinemic vasculitis or B cell malignancy.

The invention also provides methods of early treatment of cryoglobulinemic vasculitis and B cell malignancy associated with HCV in a subject. First, a sample is obtained from a subject infected with hepatitis C virus (HCV). A suitable sample is a biological fluid comprising whole blood. An anti-WA antibody is administered to the subject if the sample contains WA Xid+ B cells, thereby treating the cryoglobulinemic vasculitis and B cell malignancy associated with HCV in a subject. Preferably, the early treatment is after initial HCV infection, but prior to the manifestation of symptoms associated with cryoglobulinemic vasculitis or B cell-malignancy.

The invention also provides a method for the early detection and treatment of a subject at risk for developing B cell malignancies other than those that arise from WA B cells. First, a sample is provided from a subject infected with HCV. A suitable sample is a biological fluid comprising whole blood. Non-WA cross-idiotype positive (non-WA Xid+) B cells are detected in the sample, thereby identifying the subject as one who is at risk of developing cryoglobulinemic vasculitis and B cell malignancy associated with HCV. In one aspect, the non-WA Xid+ B cells are detected by identifying an immunoglobulin nucleic acid sequence from a clonally expanded B cell population, wherein the immunoglobulin nucleic acid sequence is associated with specific non-WA Xid. Optionally, the specific non-WA Xid+ B cells are detected with an isolated anti-non-WA Xid antibody. In one aspect, the subject is identified early. Preferably, the early-identified subject is identified after initial HCV infection, but prior to the manifestation of symptoms associated with cryoglobulinemic vasculitis or B cell malignancies.

The invention also provides a kit comprising a set of first primers and second primers, and instructions for prognosis of cryoglobulinemic vasculitis and B cell malignancy associated with HCV-infection based on the detection of the immunoglobulin nucleic acid sequences associated with WA Xid comprising IgH V1-69 or VIgH V 3-7 or related germ line genes, VK325 or VK 328, JH4 or JH3, Jk1, and SEQ ID NO: 1 or SEQ ID NO: 2. The set of first primers and second primers comprise a first primer and a second primer that flank the complementary determining region 3 (CDR3) sequence, a first primer and a second primer that flank the VH-D-JH sequence, and a first primer and a second primer that flank VK-JK sequence in Ig-encoding transcripts.

Other features and advantages of the invention will be apparent from the following description of the preferred embodiments thereof, and from the claims. Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, Genbank/NCBI accession numbers, and other references mentioned herein are incorporated by reference in their entirety. In the case of conflict, the present specification, including definitions, will control. In addition, the materials, methods, and examples are illustrative only and not intended to be limiting.

Other features and advantages of the invention will be apparent from the following detailed description and claims.

BRIEF DESCRIPTION OF THE DRAWINGS

FIG. 2 shows the results of additional studies on patient 127.

DETAILED DESCRIPTION

Figure 1:
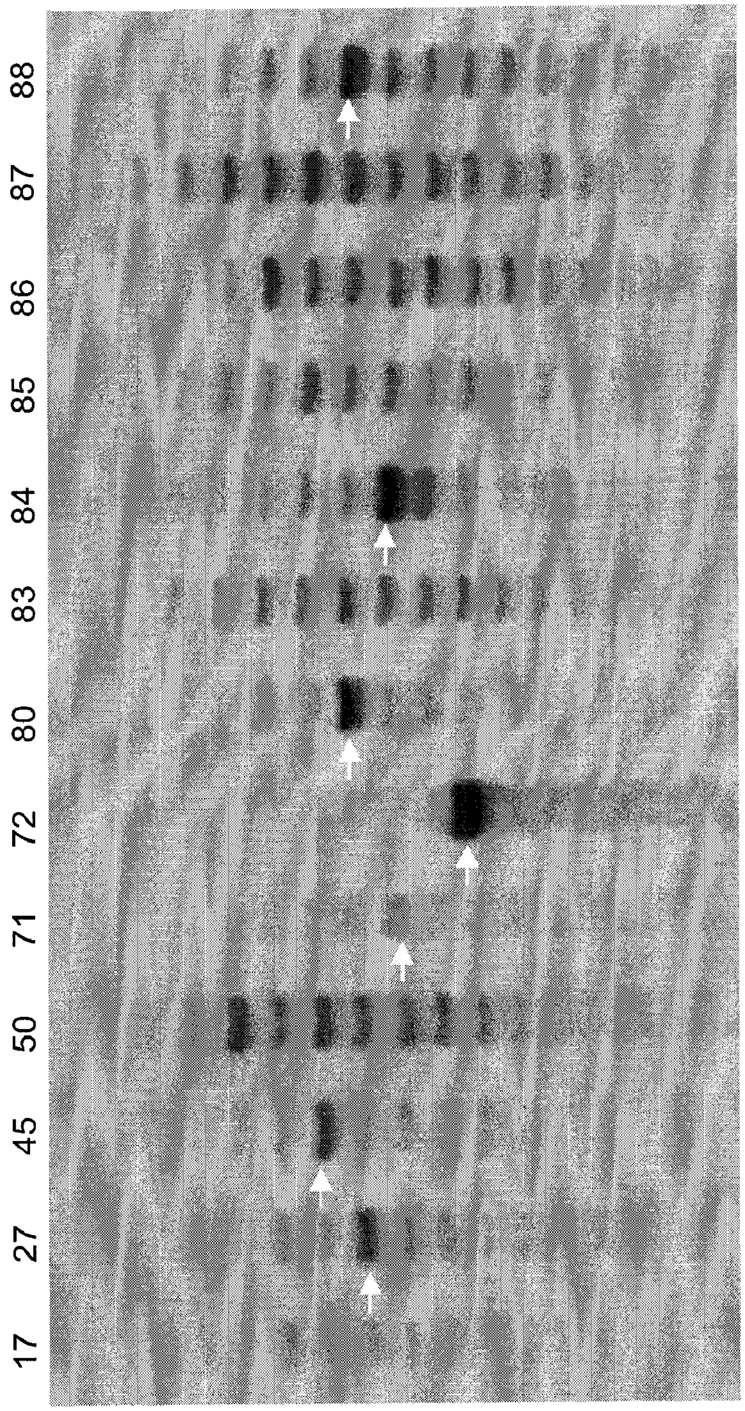
FIG. 1 is a chemilumigraph of a B cell clonal expansion analysis gel. Patient ribonucleic acid (RNA) was amplified. Patient numbers are shown at the top of each lane. Patients 27, 45, 71, 72, 80, 84, and 88 were considered positive (white arrows indicate BCE) and patients 17, 50, 83, 85, 86, and 87 were considered negative. These classifications were confirmed by densitometric scans of the gel images.
Figure 2A:
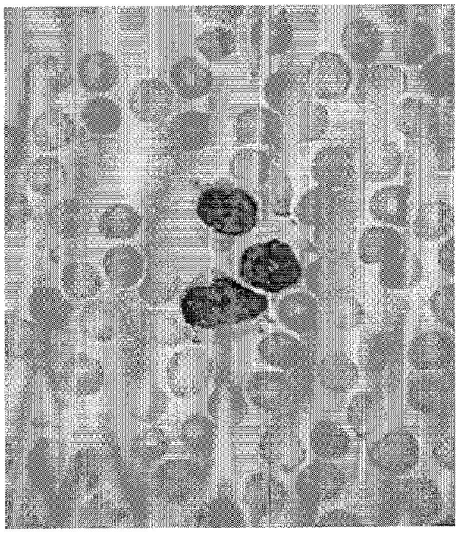
FIG. 2A is a photomicrograph of a Wright stain of peripheral blood showing villous lymphocytes.
Figure 2B:
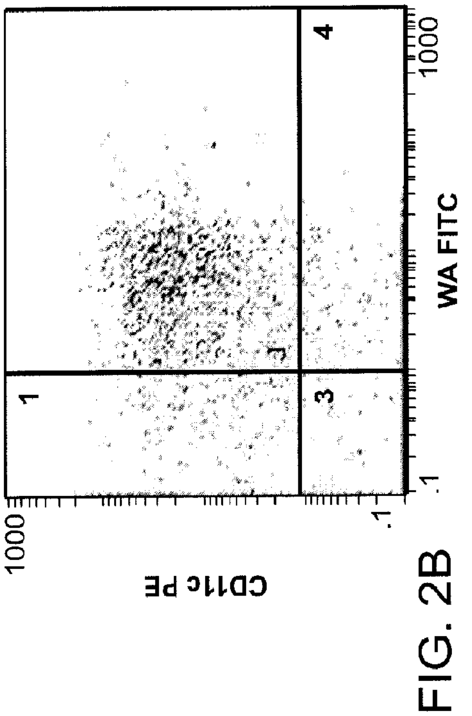
FIG. 2B is a flow cytometry histogram showing a population of CD 11c+, WA+ B cells.
Figure 2C:
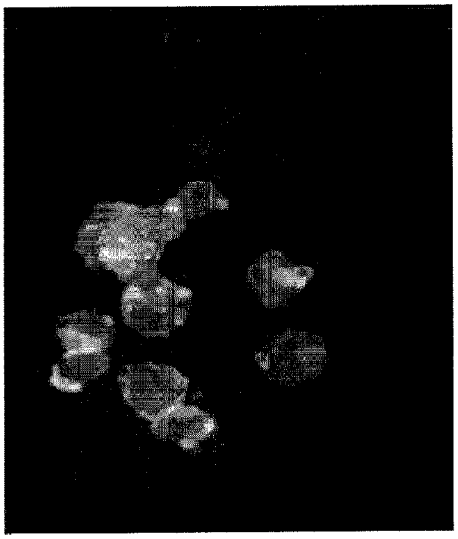
FIGS. 2C and 2D are photomicrographs depicting dual staining of CD 11C isolated cells with fluorescein isothiocyanate (FITC)-labeled anti-WA Xid (C) and phycoerythrin (PE)-labeled anti-CD11c (D).
Figure 2D:
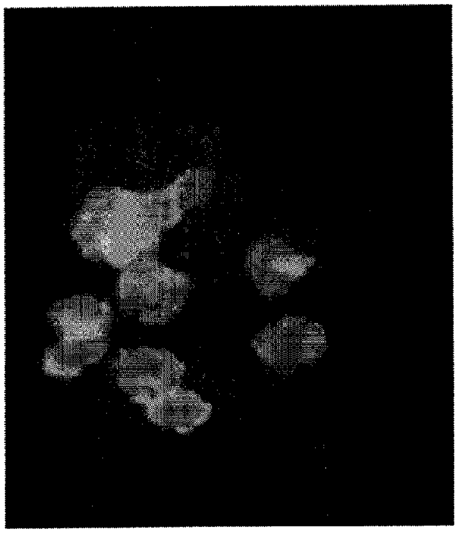

There are approximately four million patients with hepatitis C virus (HCV) infection in the United States, and over 170 million infected patients worldwide. Hepatitis C virus is a small (50-65 nm in size), enveloped, positive sense single strand ribonucleic acid (RNA) virus in the family Flaviviridae. The hepatitis C virus particle consists of a core of genetic material (RNA), surrounded by an icosahedral protective shell of protein, and further encased in a lipid (fatty) envelope of cellular origin. Two viral envelope glycoproteins, E1 and E2, are embedded in the lipid envelope. There are six major genotypes of the hepatitis C virus, which are indicated numerically, e.g., genotype 1, genotype 2, etc.

HCV is transmitted via blood-to-blood contact, e.g., injection drug use (needle-sharing), tainted blood products, and sexual transmission, and manifests as hepatitis C in humans, an infectious disease affecting the liver. Most people have few, if any, symptoms after the initial infection, yet the virus persists in the liver in about 85% of those infected. Once established, chronic infection can progress to scarring of the liver (fibrosis), and advanced scarring (cirrhosis), which is generally apparent after many years. In some cases, patients with cirrhosis develop liver failure or other complications of cirrhosis, including liver cancer. Patients who develop cirrhosis or liver cancer may require a liver transplant; however, the hepatitis C virus universally recurs after transplantation.

Acute hepatitis C refers to the first six months after infection with HCV. Between 60% and 70% of people infected with HCV are asymptomatic during the acute phase. In the minority of patients who experience acute phase symptoms, symptoms are generally mild and nonspecific, and rarely lead to a specific diagnosis of hepatitis C. Symptoms of acute hepatitis C infection include decreased appetite, fatigue, abdominal pain, jaundice, itching, and flu-like symptoms.

The hepatitis C virus is usually detectable in the blood within one to three weeks after infection by polymerase chain reaction (PCR), and antibodies to the virus are generally detectable within 3 to 15 weeks of infection. Spontaneous viral clearance rates are highly variable and between 10-60% (Caruntu F A and Benea L, 2006 J Gastrointestin Liver Dis, 15(3): 249-256) of individuals infected with HCV clear the virus from their bodies during the acute phase, as shown by normalization in liver enzymes (alanine transaminase (ALT) and aspartate transaminase (AST)), and plasma HCV-RNA clearance (known as spontaneous viral clearance). However, persistent infections are common and most patients develop chronic hepatitis C, i.e., infection persisting for more than 6 months (Villano, et al. 1999 Hepatology, 29(3): 908-914).

Chronic hepatitis C is often asymptomatic (without symptoms) and it is mostly discovered accidentally. The natural course of chronic hepatitis C varies considerably from one individual to another. Although almost all people infected with HCV have evidence of inflammation upon liver biopsy, the rate of progression of liver scarring (fibrosis) varies significantly among individuals. Factors that have been reported to influence the rate of HCV disease progression include age (associated with an increased rate of disease progression), gender (males have more rapid disease progression than females), alcohol consumption (associated with an increased rate of disease progression), HIV coinfection (associated with a markedly increased rate of disease progression), and fatty liver (the presence of fat in liver cells has been associated with an increased rate of disease progression).

Symptoms specifically suggestive of liver disease are typically absent until substantial scarring of the liver has occurred. However, hepatitis C is a systemic disease and patients may experience a wide spectrum of clinical manifestations ranging from an absence of symptoms to a more symptomatic illness prior to the development of advanced liver disease. Generalized signs and symptoms associated with chronic hepatitis C include fatigue, flu-like symptoms, joint pains, itching, sleep disturbances, appetite changes, nausea, and depression.

Once chronic hepatitis C has progressed to cirrhosis, signs and symptoms may appear that are generally caused by either decreased liver function or increased pressure in the liver circulation, a condition known as portal hypertension. Possible signs and symptoms of liver cirrhosis include ascites (accumulation of fluid in the abdomen), bruising and bleeding tendency, varices (enlarged veins, especially in the stomach and esophagus), jaundice, and a syndrome of cognitive impairment known as hepatic encephalopathy, which is due to the accumulation of ammonia and other substances normally cleared by a healthy liver.

Persistent HCV infection can be treated with medication, e.g., peginterferon and ribavirin. As the majority of people infected do not experience any symptoms during the acute phase of the disease, the diagnosis of "hepatitis C" is rarely made during the acute phase. Those who do experience acute phase symptoms are rarely ill enough to seek medical attention. The diagnosis of chronic phase hepatitis C is also challenging due to the absence of symptom specificity until advanced liver disease develops, which may not occur until decades after initial infection. Although HCV vaccines are currently under development, a vaccine against HCV does not yet exist.

Hepatitis C diagnosis begins with serological blood tests used to detect antibodies to HCV. Anti-HCV antibodies can be detected in about 80% of patients within fifteen weeks after exposure; in >90% of patients within five months after exposure; and in >97% of patients within six months after exposure. Overall, HCV antibody tests have a strong positive predictive value for exposure to the hepatitis C virus, but may miss patients who have not yet developed antibodies (seroconversion), or have an antibody level that is insufficient for reliable detection.

An uncommon manifestation of HCV infection is systemic vasculitis associated with Type II cryoglobulinemia (cryoglobulinemic vasculitis). Cryoglobulinemia is a blood disorder that is caused by abnormal proteins in the blood called cryoglobulins, which precipitate or clump together when blood is chilled and then dissolve when re-warmed. These proteins can be deposited in small and medium-sized blood vessels, which can lead to restricted blood flow to joints, muscles, and organs. The cause of cryoglobulinemia is not completely understood, but it is thought to be an autoimmune disorder (caused by the body's immune system producing antibodies that form complexes that deposit in organs and cause inflammation). The majority of cryoglobulinemia, previously designated Essential Mixed Cryoglobulinemia because the cause was not known, is now known to be caused by hepatitis C infection.

There are three types of cryglobulinemia (Type I, Type II and Type II) that are composed of immunoglobulins. Type I consists of monoclonal immunoglobulins. Type II and Type III are termed "mixed cryoglobulins", because they consist of polyclonal immunoglobulin G (IgG) and immunoglobulin M (IgM). In Type II, the IgM is monoclonal, and in Type III, the IgM is polyclonal. In both types, the IgM usually has rheumatoid factor activity. Rheumatoid factor is an antibody found in the blood of people afflicted with rheumatoid arthritis (a chronic autoimmune disease characterized by inflammation of the joints). The most common symptoms and disorders associated with cryoglobulinemia include: vasculitis, renal (kidney) disease, arthralgias and arthritis, itching, fatigue, pain, lymph node enlargement, peripheral neuropathy, stomach pain, and/or bleeding disorders.

Treatment depends on the type of cryoglobulin, underlying disease, and severity of symptoms. More extensive vasculitis associated with autoimmune diseases or essential cryoglobulinemia may respond to prednisone, cyclophosphamide, or both. Although the most effective treatment for cryoglobulinemia associated with hepatitis C has not yet been determined, brief use of prednisone followed by six months of interferon alpha has produced clinical and liver function test improvement, but relapse of liver disease and vasculitis often occurs when interferon alpha treatment is terminated.

Type II cryoglobulinemia consists of polyclonal immunoglobulin G (IgG) and monoclonal IgM rheumatoid factors (mRF), which bind to the Fc portion of an antibody to form immune complexes that contribute to the disease process. Systemic vasculitis associated with Type II cryoglobulinemia (cryoglobulinemic vasculitis) is a proliferative B cell disorder that transforms to B cell malignancy in 5-10% of patients. Eighty percent of the mRF (Casato M, et al. 1997 Blood, 90: 3865-3873) are unique because they are encoded by germ-line genes (Kunkel H G, et al. 1973 J Exp Med, 37: 331-42), and have an antibody combining site cross-idiotype (Xid) (Agnello V and Barnes J L, 1986 J Exp Med, 164: 1809-14), dubbed "WA" that is restricted to HCV-infected patients. The immunoglobulin variable region contains antigenic determinants, termed "idiotypes", which can be recognized by serological techniques (Mackworth-Young, et al. 1987 J Clin Invest, 79: 572-581). The WA cross-idiotype (Xid), the major cross-idiotype among human monoclonal rheumatoid factors (mRF), is a conformational antigenic determinant involving both H and L chains that is located in the antigen binding site (Kunkel H G, et al. 1973 J Exp Med, 137: 331; Agnello V and J L Barnes, 1986 J Exp Med, 164: 1809).

The monoclonal rheumatoid factor that bears the WA cross-idiotype (Xid) is responsible for most cryoglobulinemic vasculitis in HCV-infected patients. HCV is concentrated in the Type II cryoglobulins (Agnello V, et al. 1992 N Engl J Med, 327: 1490-1495), and production of WA mRF is driven by the virus, as anti-viral therapy induces the decline of cryoglobulinemia and the WA B cells that produce WA mRF, along with the decline in viremia (Mazzaro C, et al. 1996 Cancer, 77: 2604-13; Casato M., et al. 2002 Blood, 99: 2259-61; Hermine, et al. 2002 N Engl J Med, 347: 89-94).

The prevalence of cryoglobulinemic vasculitis is estimated at 2-5% and less than 1% of HCV-infected patients in southern Europe and the United States, respectively (Casato M and Agnello V, 2002 Mixed cryoglobulinemia syndrome secondary to hepatitis C virus infection. In: NORD Guide to Rare Disorders. 3rd ed. National Organization for Rare Disorders, editor; Lippincott Williams & Wilkins: Philadelphia, Pa.: 5). There is a much greater risk for Type II cryoglobulinemia patients to develop B cell malignancies than the overall HCV-infected population. Five to ten percent of patients with cryoglobulimemic vasculitis develop B cell malignancies (Invernizzi F, et al. 1983 Acta haematol, 70: 73-82), while 0.2 to 0.8 percent of the overall HCV-infected population (Ohsawa M, et al. 1999 J Cancer, 80: 237-239; Giordano T P, et al. 2007 JAMA, 297: 2011-17) develop B cell malignancies. Moreover, approximately 50% of B cell non-Hodgkin's lymphomas appear to arise from WA B cells (Knight G and Agnello V, 2001 Blood, 97: 3319-21; Knight G B. Gao L, Grangnani L, Elfahal M, De rosa F G, Gordon F D, Agnello V. Detectection of WA B cells in HCV infection: A potential prognostic marker for cryoglobulinemic vasculitits and B cell malignancies. Arth Rheum 2010; 62:2152).

Eighty percent of HCV-infected patients do not develop symptomatic disease. Consequently, only a small percent of these patients are treated with anti-viral therapy. The duration of HCV infection required for development of cryoglobulinemic vasculitis is not well delineated, but appears to be at least a decade (Monti G, et al. 1995 QJM, 88: 115-16). Thus, these patient are not likely to be treated before they become symptomatic unless a prognostic marker is discovered. As described in detail below, the WA B cell is a marker for Type II cryoglobulinemia and/or B cell lymphoma, and allows for early diagnosis. In addition to preventing the increased morbidity and mortality of cryoglobulinemic vasculitis and B cell malignancies, early detection and treatment of these patients before the onset of symptoms may be beneficial, as patients have greater resistance to therapy upon onset of vasculitis (Agnello V, 2000 J Rheumatol, 27: 2065-7).

As described in detail below, WA B cells were detected in asymptomatic HCV-infected patients via molecular analysis of B cell clonal expansions (BCE). Early detection of B cell proliferation is determined via reverse transcription polymerase chain reaction (RT-PCR) to detect the Ig gene rearrangements that constitute the normal B cell repertoire in the blood. In this manner, expanded B cell clones are detected, e.g., over-expressed B cell clones in Type II cryoglobulinemia or B cell malignancy. The WA B cell clonal expansions (BCE) are identified via sequence analysis of the BCE utilizing the established extensive criteria for the Ig genes encoding WA mRF (Knight G B, et al. 1993 J Exp Med, 178: 1903-11).

EXAMPLE 1

WA B Cells in Asymptomatic HCV Infected Patients are a Marker for the Development of Cryoglobulinemic Vasculitis and Associated B Cell Malignancies Briefly, asymptomatic HCV-infected patients, HCV-negative patients, and control patients with cryoglobulinemic vasculitis negative and positive for WA mRF were examined. BCE were isolated, sequenced, and WA BCE identified. As described in detail below, BCE were detected in all positive control patients with cryoglobulinemic vasculitis; however, only HCV-infected patients had WA BCE. None of the 33 control HCV-negative patients had a BCE. WA BCE were detected in four of 55 patients (7.4%) with asymptomatic HCV infection; none of 14, and five of 37 in HCV-infected patients with Type III cryoglobulinemia and serum RF, respectively. One patient with a WA BCE had asymptomatic splenic lymphoma with villous lymphocytes, which were WA B cells.

Asymptomatic HCV-infected patients, HCV-negative patients, and control patients with cryoglobulinemic vasculitis negative and positive for WA mRF were examined. Blood specimens for B cell clonal analysis were obtained from consecutive asymptomatic patients with and without HCV infection that consented to the study in the Gastroenterology clinic at the Lahey Clinic (Burlington, Mass.) over a six month period. HCV-infected patients had not received anti-viral treatment or chemotherapy. Patients with cryoglobulinemic vasculitis or Type III cryoglobulinemia were recruited from various departments at the Lahey Clinic. Blood samples on asymptomatic HCV-infected patients with RF, but without cryoglobulinemia were obtained in a two year follow-up study performed in the Hepatitis Clinic at the Veterans Affairs Medical Center (VAMC; Bedford, Mass.). Medical records were reviewed to determine the demographic characteristics of the patients, the presence of cryoglobulinemic vasculitis or other extrahepatic disease manifestations and the presence of cirrhosis.

The presence of one of the following was required for the diagnosis of cryoglobulinemic vasculitis: palpable purpura, peripheral neuropathy, renal disease, or biopsy proven medium-sized vessel vasculitis. Renal disease criteria included the presence of one of the following: proteinuria >500 mg/die, nephrotic syndrome, glomerulonephritis, acute or chronic renal failure, serum creatinine >1.5 mg/dl. Renal disease due to other diseases (e.g., diabetes mellitus or systemic lupus erythematosus) was excluded. Peripheral neuropathy was diagnosed by a neurologist, with or without confirmation by electrophysiological parameters. Peripheral neuropathy secondary to other diseases, such as diabetes mellitus or alcoholism was excluded. HCV antibodies, HCV RNA detection and quantification, and cryoglobulin isolation, quantification and typing were performed as previously described (De Rosa F G and Agnello V, 2009 J Rheumatol, 36: 1953). Patients with HCV-negative cryoglobulinemic vasculitis of unknown etiology were studied repeatedly for serum and cryoglobulin HCV antibodies and HCV RNA to confirm the absence of HCV infection. Alanine aminotransferase (Alt, normal range, 7-40 IU/ml) and rheumatoid factor (RF, normal range, <20 IU/ml) studies were performed in the clinical laboratory. Peripheral blood mononuclear cells (PBMC) were isolated from heparinized blood by routine Ficoll density gradient centrifugation.

Additional analysis was performed on samples from patient 127. Hematological tests and immuno-phenotyping of lymphocytes were performed in the clinical laboratory. CD $11c^+$ lymphocytes (a phenotypic marker for villous lymphocytes (Liu X, et al. 2003 J Huazhong Univ Sci Technolog Med Sci, 23: 236-8) were isolated as follows: PBMC were incubated with mouse anti-CD 11c (Beckman Coulter; Fullerton, Calif.) for 30 minutes at 4° C., washed and incubated with Dynabeads goat anti-mouse Ig magnetic beads (Invitrogen Corp; Carlsbad, Calif.) for 30 minutes at 4° C. $CD11c^+$ cells were captured by a magnet, washed and cultured overnight at 37° C. to dissociate the attached magnetic beads. After incubation, the beads were removed from the cells with a magnet. The isolated cells were stained with fluourocein isothiocyanate (FITC) labeled anti-WA mRF and phycoerythrin (PE) labeled anti-CD 11c, and examined by fluorescent microscopy and flow cytometry.

Detection and Analysis of BCE

The immunoglobulin heavy chain locus rearranges during B cell development to juxtapose the $V_H$, D, and J regions that constitute the third complementary determining region (CDR3) of the variable part of the heavy chain. During the rearrangement process, nucleotide additions and deletions occur at the $V_H$-D (N) and D-J (P) junctions. The diversity of the CDR3 region heavy chain genes was assessed in the mRNA by performing RT-PCR using primers that flank this region. The resultant products were resolved on sequencing gels and in the normal repertoire represent a normal distribution of fragment lengths differing by three nucleotides, or one codon, around the average length of the CDR3. In the case of a monoclonal expansion of a particular B cell clone, as may occur in Type II cryoglobulinemia, a band on a sequencing gel may appear over-expressed. The observed clonally expanded bands were excised from the sequencing gel and subjected to direct cycle sequencing. Sequences were compared to known Ig sequences in GenBank.

WA mRF are predominantly products of the IGKV3-20 (Kv325) light chain gene and a $V_H1$ gene including IGHV1-69 and related germ-line genes, although a $V_H3$ gene (IGHV3-7) may be used (Knight G B, et al. 1993 J Exp Med, 178: 1903-11). The D regions have two types of sequence features. Consensus 1 (SEQ ID NO: 1), the 9-11 amino acid region beginning with glutamic acid and ending in proline that is associated with the IGHV1-69 gene and usually $J_H4$, appears to be from the IGHD4-17 gene (Knight G B, et al. 1993 J Exp Med, 178: 1903-11). Consensus 2 (SEQ ID NO: 2) originally found in a VH3-7 containing WA RF, M7 (Pinheiro G, et al. 1993 Genbank accession numbers, UO3400 and UO3401), and later was found associated with other $V_H3$-7 RF combined with $J_H3$ and IGKV3-15 (kv328) (Borretzen M, et al. 1995 J Immunol, 155: 3630-7).

Total cell RNA was isolated from peripheral blood monocyte cells (PBMC) by extraction with TRIzol® (Life Technologies), or Rneasy RNA extraction kit (QIAGEN). RT-PCR was performed as previously described (Knight G B, et al. 1993 J Exp Med, 178: 1903-1911). Initial fingerprint screens to examine CDR3 diversity were performed using primers from a conserved region in FW3 and the μ-constant region. VH-D-JH PCR products were obtained using upstream oligonucleotides from the VH leader and FW1 regions with the constant region primer. VK-JK fragments were amplified using upstream oligonucleotides from the VK leader and downstream primer from the K constant region. One primer in each RT-PCR was labeled with biotin, for isolation of the amplicons, or 6-FAM, for rapid screening for oligoclonal bands using an ABI 377 automated DNA sequencer and GeneScan® software. The PCR products were electrophoretically separated on 6% sequencing gel, transferred to Tropilon-plus membranes (Tropix) by capillary transfer, and detected by chemiluminescence. The observed clonally expanded bands on the chemilumigraph were excised and purified from the sequencing gel. The genes of monoclonal expanded Ig were subjected to direct cycle sequencing using an ABI 377 automated DNA sequencer with Big Dye terminators or biotin chemiluminescence (Phototope-star, New England Biolabs). Comparisons of the deduced amino acid sequences of Ig genes obtained and Ig sequences in the GenBank database were analyzed using the BLAST server at NCBI.

Statistical Analysis

Demographic and clinical characteristics were summarized for each group and presented as frequencies (gender) and means and standard deviations (continuous variables). The number of patients with BCE and WA BCE were also tabulated and prevalences of each expansion type were compared between key groups of interest using Fisher's exact tests. A p-value of ≤0.05 was used as the threshold to conclude prevalences significantly differed between groups.

Demographic and laboratory data are summarized in Table 1 below. The BCE methodology was tested employing positive and negative control specimens from ten patients with cryoglobulinemic vasculitis. The positive and negative control groups consisted of six HCV-infected patients (HCV+, Type II) and four HCV-negative patients (HCV−, Type II), respectively (Table 2). BCE were found in all patients in both groups as expected for patients with cryoglobulinemic vasculitis. WA BCE were identified by sequence analysis of the BCE detected (FIG. 1, Table 3). Four of the six patients in the HCV+, Type II group had WA BCE; this finding was consistent with the previously reported prevalence of WA mRF in HCV-infected patients with cryoglobulinemic vasculitis (Casato M, et al. 1997 Blood, 90: 3865-3873). None of the HCV−, Type II group had a WA BCE which confirmed the restriction of WA mRF to HCV-infected patients.

TABLE 1

Clinical and laboratory data on patients

| Patients | Sex F/M | Age* | Alt* | HCV* |
|---|---|---|---|---|
| HCV+, Type II | 1/5 | 54.8 (10.2) | 47.5 (22.9) | 17.8 (38.4) × $10^6$ |
| HCV−, Type II | 3/1 | 64.0 (14.0) | 17.7 (2.0) | NA |
| HCV+ | 16/39 | 43.0 (7.0) | 98.0 (83.0) | 9.8 (16.0) × $10^6$ |
| HCV− | 16/17 | 42.3 (11.0) | 36.0 (32.5) | NA |
| HCV+, RF | 0/37 | 51.8 (6.6) | 127.9 (126.27) | 2.8 (4.6) × $10^6$ |
| HCV+, Type III | 5/9 | 49.6 (8.0) | 114.8 (87.9) | 3.3 (4.3) × $10^6$ |

*mean (1 standard deviation)

TABLE 2

Detection of BCE in HCV-infected patients and controls

| Patients | Number | BCE | WA BCE |
|---|---|---|---|
| HCV+, Type II | 6 | 6 | 4 |
| HCV−, Type II | 4 | 4 | 0 |
| HCV+ | 55 | 9 | 4 |
| HCV− | 33 | 0 | 0 |
| HCV+, RF | 37 | 7 | 5 |
| HCV+, Type III | 14 | 1 | 0 |

TABLE 3

Identification of WA BCE by nucleic acid sequence analyses

| | CLONE | D REGION | VH | JH | VK | JK |
|---|---|---|---|---|---|---|
| CONSENSUS 1 | | EG-------NP (SEQ ID NO: 1) | | | | |
| HCV+ | 7 | EGGDSSDYYY (SEQ ID NO: 3) | IGHV1-69 | 4 | IGKV3-20 | 1 |
| | 27 | EQDSDSSAYY (SEQ ID NO: 4) | IGHV1-69 | 4 | IGKV3-20 | 1 |
| | 45 | EGGLTVTNP (SEQ ID NO: 5) | IGHV1-69 | 4 | IGKV3-20 | 1 |
| HCV+, type II | 1 | EGRANDYSNP (SEQ ID NO: 6) | IGHV1-69 | 4 | IGKV3-20 | 1 |
| | 57 | EGRLTVTNP (SEQ ID NO: 7) | IGHV1-69 | 4 | IGKV3-20 | 1 |
| | 118 | EGRLTVTNP (SEQ ID NO: 8) | IGHV1-69 | 4 | IGKV3-20 | 2 |
| HCV+, RF+ | 127 | EGRGYSGSDP (SEQ ID NO: 9) | — | — | — | — |
| | 137 | EFSSDSSGYY (SEQ ID NO: 10) | — | — | — | — |
| | 146 | EGRGYSGSDP (SEQ ID NO: 11) | — | — | — | — |
| | 148 | EFSSDSSGYY (SEQ ID NO: 12) | — | — | — | — |
| CONSENSUS 2 | | GDYYD-S-G-YIDA (SEQ ID NO: 2) | | | | |
| HCV+ | 80 | GDRYYYGYYG (SEQ ID NO: 13) | IGHV1-69 | 4 | IGKV3-20 | 2 |
| HCV+, II | 18 | GHDTSDYYSPY (SEQ ID NO: 14) | IGHV1-69 | 4 | IGKV3-20 | 1 |
| HCV+, RF+ | 141 | DYGEQREGYYY (SEQ ID NO: 15) | — | — | — | — |

TABLE 3-continued

| Identification of WA BCE by nucleic acid sequence analyses | | | | | | |
|---|---|---|---|---|---|---|
| | CLONE | D REGION | VH | JH | VK | JK |
| OTHER (non-WA) | | | | | | |
| HCV+ | 14 | AGYDFWSGYYSLDYWY (SEQ ID NO: 16) | IGHV1-69 | 4 | IGKV3-20 | 1 |
| | 84 | AGEMATNRPQA (SEQ ID NO: 17) | IGHV1-69 | 3 | IGKV3-20 | 2 |
| | 88 | GWGGAGTTTP (SEQ ID NO: 18) | IGHV1-69 | 4 | IGKV3-20 | 2 |
| HCV+, type II | 38 | DGGTGS (SEQ ID NO: 19) | IGHV1-69 | 4 | IGKV3-15 | 1 |
| HCV−, type II | 11 | GSSDCSMSQLP (SEQ ID NO: 20) | IGHV1-69 | 4 | IGKV3-20 | 2 |
| | 113 | LHYGSGSYYS (SEQ ID NO: 21) | IGHV1-69 | 4 | IGKV3-20 | 1 |
| HCV+, type III | 97 | PXADSXDVAWT (SEQ ID NO: 22) | IGHV1-69 | 3 | IGKV3-20 | 1 |
| HCV+, RF+ | 133 | GGYCSGGSYY (SEQ ID NO: 23) | — | — | — | — |
| | 138 | GKTRGNFDY (SEQ ID NO: 24) | — | — | — | — |

To determine if WA BCE could be detected in asymptomatic HCV-infected patients, a group of 55 asymptomatic HCV-infected patients (HCV+) and a group of 33 HCV negative patients (HCV−) were examined. BCE were detected in nine (14%) patients in the HCV+ group. Four patients in this group (7.4%) had WA BCE. Neither cryoglobulins, nor RF was detected in the sera of these patients. A review of the medical records confirmed that none of the patients had cryoglobulinemic vasculitis or other extrahepatic symptoms. Of the five patients with non-WA BCE: one patient had neither cryoglobulins or RF; one patient had RF negative Type II cryoglobulinemia that is not associated with cryoglobulinemic vasculitis (De Rosa F G and Agnello V, 2009 J Rheumatol, 36: 1953); and three patients had weakly positive serum RF (21.7, 23.7, 40.9 IU/ml). None of the patients in the HCV− negative group had a BCE.

None of the patients with WA BCE were symptomatic, but in one patient (patient 127, Table 3), villous lymphocytes were present in the peripheral blood, and the B lymphocyte phenotype was consistent with splenic lymphoma, although there were no clinical signs or symptoms of lymphoma. Immunophenotyping showed a monoclonal population of B cells that were IgM+, K+, IgD−, CD19+, CD 5−, CD10−, CD23−, CD11c+, WA+. Villous lymphocytes comprised 5% of the peripheral lymphocytes. Since villous lymphocytes are associated with the CD11c, the CD11c lymphocytes were isolated from the patient's (patient 127) peripheral lymphocytes. Flow cytometry and fluorescent microscopy studies demonstrated a monoclonal population of WA+, CD11c+ B cells that appeared to be villous lymphocytes (FIG. 2). This finding suggested that some villous lymphocytes may be WA B cells.

Nucleic acid sequence analyses were performed on 22 of the 27 BCE (Table 3). Five BCE could not be analyzed because of contaminating sequences. Thirteen of the 22 BCE had WA sequences. Ten had the consensus 1 D region sequence and three had the consensus 2 sequence. Two of the latter were recombined with IGHV1-69 rather than IGHV3-7. One BCE had a IGKV3-15 light chain sequence; the rest had the most common light chain sequence found in WA mRF, IGKV3-20. There were seven sequences other than WA; all seven had Ig genes similar to WA except for the D region genes. There were no homologies to any known RF or to the anti-HCV E2 envelope protein E2, the only other monoclonal protein identified in HCV infection (Quinn E R, et al. 2001 Blood, 98: 3745-49). Four exhibited no significant D region homology with any known Ig sequence in GenBank, one showed weak homology with an Ig found in memory B cells (Stein K, et al. 1999 Blood, 94: 2800-8) and two had significant homology with a fetal Ig (Zemlin M, et al. 2001 Blood, 97: 1511-13).

It is hypothesized that with increased duration of HCV infection, mRF result from transition of polyclonal RF to Type III cryoglobulins (polyclonal IgG and polyclonal IgM RF) to Type II cryoglobulins (Lunel F, et al. 1994 Gastroenterology, 106: 1291-300; Schifferli J A, et al. 1995 Adv Nephrol Necker Hosp, 24: 107-29). This "transition" hypothesis predicts an increased prevalence of WA BCE in patients with RF and in patients with Type III cryoglobulinemia compared to patients with neither RF, nor cryoglobulinemia.

To determine if the WA BCE prevalence was increased among HCV-infected patients with RF, a group of 37 asymptomatic HCV-infected patients with RF in the blood, but without cryoglobulinemia (HCV+, RF) was examined (Table 2). Seven patients (18.9%) in this group had BCE and five (13.5%) had WA BCEs. The prevalence of BCE and WA BCE in HCV+, RF group was not significantly greater than in the HCV+ group (p=0.78 and p=0.48 for BCE and WA BCE, respectively).

To determine if an increased prevalence of BCE and WA BCEs was present among HCV-infected patients with Type III cryoglobulinemia (HCV+, Type III), 14 patients with Type III cryoglobulins were examined (Table 2). Only one had a BCE; a non-WA BCE. The prevalence of BCE and WA BCE in the HCV+, Type III group was not significantly greater than in the HCV+ group (p=0.67 and p=0.58 for BCE and WA B cells, respectively).

The detection of WA BCE in asymptomatic HCV-infected patients indicates that the WA B cell is a marker for the development of cryoglobulinemic vasculitis and B cell malignancies. As described above, in support of this contention, the WA B cell marker was detected in a patient (patient 127) with a monoclonal B cell population consistent with splenic lymphoma with villous lymphocytes. Assuming this patient progressed to clinical splenic lymphoma, the odds of finding such a patient by chance is approximately one in 10 million if the following prevalences are independent: HCV infection in the United States (approximately 1%), the prevalence of WA BCE in HCV infection (7.5%), the prevalence of non-Hodgkins lymphoma (NHL) (0.1%) and splenic lymphoma (less than 15% of NHL). This patient was also informative because the villous lymphocytes in the blood were WA B cells. It is hypothesized that splenic lymphoma with villous lymphocytes is associated with Type II cryoblobulinemia and HCV infection (Saadoun D, et al. 2005 Blood, 105: 74-6). The results presented above indicate that the villous lymphocytes in some splenic lymphomas in HCV-infected patients are WA B cells.

WA BCE accounted for approximately half of the BCE detected in HCV-infected patients. The non-WA BCE sequences were not identified. They were not related to RF, as there were no significant D region homology to any known RF. Also, they were not related to the only monoclonal protein other than WA mRF identified in HCV infection, anti-HCV envelope protein E2 (Quinn E R, et al. 2001 Blood, 98: 3745-49). Although there were no D region homologies, all the other Ig genes in the non-WA BCE were similar to WA genes. The Ig genes encoding WA mRF are utilized in innate host defense immunoglobulin responses. These genes are also found in fetal and B cell memory Ig repertoires (Klein U, et al. 1997 Blood, 89: 1288-98) which may explain the homologies to these immunoglobulins found in three of the non-WA BCE. The most likely explanation for etiology of the BCE in HCV infection is that there is a wide variety of innate immunoglobulins produced in this infection that are stimulated and expand with the prolonged duration of infection that is characteristic of the disease.

In a previous study, RF was present in the sera of all HCV-infected patients with BCEs which led the authors to conclude the clones produced RF (Franzin F, et al. 1995 Br J Haematol, 90: 548-52). In this study, the detection of BCE in the sera of patients without RF and the detection of BCEs without significant homology to RF in patients with RF argue against that conclusion. In addition, in the same study, BCE were not detected in HCV-infected patients with Type III cryoglobulins. The latter finding, taken together with the findings in this study provide evidence against the widely held notion that Type II cryoglobulins arise from Type III cryoglobulins.

Currently, approximately 2% of HCV-infected patients are treated with anti-viral therapy (Volk M L, et al. 2009 Hepatol, 50: 1750-55). The odds that a patient that will develop cryoglobulinemic vasculitis or B cell malignancy receives anti-viral therapy are less than one in a five hundred and one in a five thousand, respectively. Automated high through-put sequencers make clinical application of the methodology described herein feasible. For example, routine genotyping of HCV is performed by cost effective, high through-put sequence analysis. Moreover, methods for detecting the WA Xid using an anti-WA Xid antibody (as described for patient 127, above) may provide a simpler, clinically applicable, methodology.

In this study, 56% of BCE detected in HCV-infected patients were WA BCE, which may be a reasonable estimate of the prevalence of WA B cell malignancies among HCV-infected patients. Currently, only the WA Xid has been identified among B cell malignancies; 25% of NHL associated with HCV infection were WA B cells. It is likely that most, if not all Wallenstrom's macroglobulinemia and splenic lymphomas associated with HCV infection are derived from WA B cells (Agnello V, et al. 1992 N Engl J Med, 327: 1490-5; Casato M, et al. 2002 Blood, 99: 2259-61). The method of Xid analysis described above identifies other BCE that progress to B cell malignancies when out-come studies on larger populations are performed.

The methods described herein allow for the identification and treatment of asymptomatic HCV patients with BCE. The methods described herein also allow for the early detection of WA B cells and other B cell proliferation, which is useful in preventing and treating cryoglobulinemic vasculitis and B cell malignancies in HCV-infected patients. The identification of Xid among B cell malignancies in these patients also provides an alternative treatment modality. For example, monoclonal (mAb) anti-Xid is used as a therapeutic agent, e.g., anti-WA mAb is used to treat WA B cell malignancies not responsive to anti-viral therapy.

OTHER EMBODIMENTS

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. Genbank and NCBI submissions indicated by accession number cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method for detecting an over-expressed immunoglobulin nucleic acid sequence from a clonally expanded B cell population in a subject comprising (a) providing a cDNA sample from the subject, wherein the subject is infected with hepatitis C virus (HCV) but is asymptomatic for cryoglobulinemic vasculitis and B cell malignancy; (b) contacting the sample with a set of first primers and second primers wherein said set of first primers and second primers comprises a first primer and a second primer that flank the complementary determining region 3 (CDR3) sequence, a first primer and a second primer that flank a VH-D-JH sequence and a first primer and a second primer that flank a VK-JK sequence in Ig-encoding transcripts; (c) amplifying said CDR3 sequence, said VH-D-JH sequence, and said VK-JK sequence; and (d) detecting an overexpressed nucleic acid sequence encoding an amino acid sequence comprising IgH V1-69 or IgHV V 3-7, VK325 or VK 328, JH4 or JH3, Jk1, and a D region consensus sequence comprising SEQ ID NO: 1 or SEQ ID NO: 2.

2. The method of claim 1, wherein said sample is a biological fluid comprising whole blood.

3. The method of claim 1, wherein the subject is in the acute phase of HCV infection.

4. The method of claim 1, wherein the subject has not received anti-viral treatment or chemotherapy.

5. The method of claim 1, further comprising treating the subject with prednisone, cyclophosphamide, or both, following step (d).

* * * * *

SEQUENCE LISTING

```
<160> NUMBER OF SEQ ID NOS: 24

<210> SEQ ID NO 1
<211> LENGTH: 11
<212> TYPE: PRT
<213> ORGANISM: Artificial Sequence
<220> FEATURE:
<223> OTHER INFORMATION: D Region consensus sequence
<220> FEATURE:
<221> NAME/KEY: MISC_FEATURE
<222> LOCATION: (3)..(9)
<223> OTHER INFORMATION: Wherein Xaa is any amino acid.

<400> SEQUENCE: 1

Glu Gly Xaa Xaa Xaa Xaa Xaa Xaa Xaa Asn Pro
1               5                   10
```

-continued

<210> SEQ ID NO 2
<211> LENGTH: 14
<212> TYPE: PRT
<213> ORGANISM: Artificial Sequence
<220> FEATURE:
<223> OTHER INFORMATION: Consensus D Region
<220> FEATURE:
<221> NAME/KEY: MISC_FEATURE
<222> LOCATION: (6)..(6)
<223> OTHER INFORMATION: Wherein Xaa is any amino acid.
<220> FEATURE:
<221> NAME/KEY: MISC_FEATURE
<222> LOCATION: (8)..(8)
<223> OTHER INFORMATION: Wherein Xaa is any amino acid.
<220> FEATURE:
<221> NAME/KEY: MISC_FEATURE
<222> LOCATION: (10)..(10)
<223> OTHER INFORMATION: Wherein Xaa is any amino acid.

<400> SEQUENCE: 2

```
Gly Asp Tyr Tyr Asp Xaa Ser Xaa Gly Xaa Tyr Ile Asp Ala
1               5                   10
```

<210> SEQ ID NO 3
<211> LENGTH: 10
<212> TYPE: PRT
<213> ORGANISM: Artificial Sequence
<220> FEATURE:
<223> OTHER INFORMATION: HCV+ D Region

<400> SEQUENCE: 3

```
Glu Gly Gly Asp Ser Ser Asp Tyr Tyr Tyr
1               5                   10
```

<210> SEQ ID NO 4
<211> LENGTH: 10
<212> TYPE: PRT
<213> ORGANISM: Artificial Sequence
<220> FEATURE:
<223> OTHER INFORMATION: HCV+ D Region

<400> SEQUENCE: 4

```
Glu Gln Asp Ser Asp Ser Ser Ala Tyr Tyr
1               5                   10
```

<210> SEQ ID NO 5
<211> LENGTH: 9
<212> TYPE: PRT
<213> ORGANISM: Artificial Sequence
<220> FEATURE:
<223> OTHER INFORMATION: HCV+ D Region

<400> SEQUENCE: 5

```
Glu Gly Gly Leu Thr Val Thr Asn Pro
1               5
```

<210> SEQ ID NO 6
<211> LENGTH: 10
<212> TYPE: PRT
<213> ORGANISM: Artificial Sequence
<220> FEATURE:
<223> OTHER INFORMATION: HCV+, type II D Region

<400> SEQUENCE: 6

```
Glu Gly Arg Ala Asn Asp Tyr Ser Asn Pro
1               5                   10
```

<210> SEQ ID NO 7

-continued

<211> LENGTH: 9
<212> TYPE: PRT
<213> ORGANISM: Artificial Sequence
<220> FEATURE:
<223> OTHER INFORMATION: HCV+, type II D Region

<400> SEQUENCE: 7

Glu Gly Arg Leu Thr Val Thr Asn Pro
1 5

<210> SEQ ID NO 8
<211> LENGTH: 9
<212> TYPE: PRT
<213> ORGANISM: Artificial Sequence
<220> FEATURE:
<223> OTHER INFORMATION: HCV+, type II D Region

<400> SEQUENCE: 8

Glu Gly Arg Leu Thr Val Thr Asn Pro
1 5

<210> SEQ ID NO 9
<211> LENGTH: 10
<212> TYPE: PRT
<213> ORGANISM: Artificial Sequence
<220> FEATURE:
<223> OTHER INFORMATION: HCV+, RF+ D Region

<400> SEQUENCE: 9

Glu Gly Arg Gly Tyr Ser Gly Ser Asp Pro
1 5 10

<210> SEQ ID NO 10
<211> LENGTH: 10
<212> TYPE: PRT
<213> ORGANISM: Artificial Sequence
<220> FEATURE:
<223> OTHER INFORMATION: HCV+, RF+ D Region

<400> SEQUENCE: 10

Glu Phe Ser Ser Asp Ser Ser Gly Tyr Tyr
1 5 10

<210> SEQ ID NO 11
<211> LENGTH: 10
<212> TYPE: PRT
<213> ORGANISM: Artificial Sequence
<220> FEATURE:
<223> OTHER INFORMATION: HCV+, RF+ D Region

<400> SEQUENCE: 11

Glu Gly Arg Gly Tyr Ser Gly Ser Asp Pro
1 5 10

<210> SEQ ID NO 12
<211> LENGTH: 10
<212> TYPE: PRT
<213> ORGANISM: Artificial Sequence
<220> FEATURE:
<223> OTHER INFORMATION: HCV+, RF+ D Region

<400> SEQUENCE: 12

Glu Phe Ser Ser Asp Ser Ser Gly Tyr Tyr
1 5 10

<210> SEQ ID NO 13
<211> LENGTH: 10

-continued

```
<212> TYPE: PRT
<213> ORGANISM: Artificial Sequence
<220> FEATURE:
<223> OTHER INFORMATION: HCV+ D Region

<400> SEQUENCE: 13

Gly Asp Arg Tyr Tyr Tyr Gly Tyr Tyr Gly
1               5                   10


<210> SEQ ID NO 14
<211> LENGTH: 11
<212> TYPE: PRT
<213> ORGANISM: Artificial Sequence
<220> FEATURE:
<223> OTHER INFORMATION: HCV+, II D Region

<400> SEQUENCE: 14

Gly His Asp Thr Ser Asp Tyr Tyr Ser Pro Tyr
1               5                   10


<210> SEQ ID NO 15
<211> LENGTH: 11
<212> TYPE: PRT
<213> ORGANISM: Artificial Sequence
<220> FEATURE:
<223> OTHER INFORMATION: HCV+, RF+ D Region

<400> SEQUENCE: 15

Asp Tyr Gly Glu Gln Arg Glu Gly Tyr Tyr Tyr
1               5                   10


<210> SEQ ID NO 16
<211> LENGTH: 16
<212> TYPE: PRT
<213> ORGANISM: Artificial Sequence
<220> FEATURE:
<223> OTHER INFORMATION: HCV+ D Region

<400> SEQUENCE: 16

Ala Gly Tyr Asp Phe Trp Ser Gly Tyr Tyr Ser Leu Asp Tyr Trp Tyr
1               5                   10                  15


<210> SEQ ID NO 17
<211> LENGTH: 11
<212> TYPE: PRT
<213> ORGANISM: Artificial Sequence
<220> FEATURE:
<223> OTHER INFORMATION: HCV+ D Region

<400> SEQUENCE: 17

Ala Gly Glu Met Ala Thr Asn Arg Pro Gln Ala
1               5                   10


<210> SEQ ID NO 18
<211> LENGTH: 10
<212> TYPE: PRT
<213> ORGANISM: Artificial Sequence
<220> FEATURE:
<223> OTHER INFORMATION: HCV+

<400> SEQUENCE: 18

Gly Trp Gly Gly Ala Gly Thr Thr Thr Pro
1               5                   10


<210> SEQ ID NO 19
<211> LENGTH: 6
<212> TYPE: PRT
```

-continued

<213> ORGANISM: Artificial Sequence
<220> FEATURE:
<223> OTHER INFORMATION: HCV+, type II D Region

<400> SEQUENCE: 19

Asp Gly Gly Thr Gly Ser
1 5

<210> SEQ ID NO 20
<211> LENGTH: 11
<212> TYPE: PRT
<213> ORGANISM: Artificial Sequence
<220> FEATURE:
<223> OTHER INFORMATION: HCV-, type II D Region

<400> SEQUENCE: 20

Gly Ser Ser Asp Cys Ser Met Ser Gln Leu Pro
1 5 10

<210> SEQ ID NO 21
<211> LENGTH: 10
<212> TYPE: PRT
<213> ORGANISM: Artificial Sequence
<220> FEATURE:
<223> OTHER INFORMATION: HCV-, type II D Region

<400> SEQUENCE: 21

Leu His Tyr Gly Ser Gly Ser Tyr Tyr Ser
1 5 10

<210> SEQ ID NO 22
<211> LENGTH: 11
<212> TYPE: PRT
<213> ORGANISM: Artificial Sequence
<220> FEATURE:
<223> OTHER INFORMATION: HCV+, type III D Region
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid

<400> SEQUENCE: 22

Pro Xaa Ala Asp Ser Xaa Asp Val Ala Trp Thr
1 5 10

<210> SEQ ID NO 23
<211> LENGTH: 10
<212> TYPE: PRT
<213> ORGANISM: Artificial Sequence
<220> FEATURE:
<223> OTHER INFORMATION: HCV+, RF+ D Region

<400> SEQUENCE: 23

Gly Gly Tyr Cys Ser Gly Gly Ser Tyr Tyr
1 5 10

<210> SEQ ID NO 24
<211> LENGTH: 9
<212> TYPE: PRT

-continued

```
<213> ORGANISM: Artificial Sequence
<220> FEATURE:
<223> OTHER INFORMATION: HCV+, RF+ D Region

<400> SEQUENCE: 24

Gly Lys Thr Arg Gly Asn Phe Asp Tyr
1               5
```